(12) United States Patent
Murakado et al.

(10) Patent No.: US 6,203,804 B1
(45) Date of Patent: Mar. 20, 2001

(54) EXTERNAL SKIN-CARE COMPOSITION

(75) Inventors: Chie Murakado; Kazuhiro Yamaki, both of Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/179,890

(22) Filed: Oct. 28, 1998

(30) Foreign Application Priority Data

Oct. 28, 1997 (JP) ................................... 9-295433

(51) Int. Cl.$^7$ ................................................ A61K 6/00
(52) U.S. Cl. .................. 424/401; 536/123.1; 514/944; 514/780; 514/781
(58) Field of Search .............. 424/401; 536/123.1; 514/944, 780, 781

(56) References Cited

U.S. PATENT DOCUMENTS

| | | |
|---|---|---|
| 4,291,025 | 9/1981 | Pellico .......................... 424/180 |
| 5,385,729 * | 1/1995 | Prencipe et al. .................. 424/70.11 |
| 5,502,181 * | 3/1996 | Kojima et al. ..................... 536/123.1 |
| 5,961,990 * | 10/1999 | Delrieu et al. ...................... 424/401 |

FOREIGN PATENT DOCUMENTS

| | | |
|---|---|---|
| 406056625 * | 3/1994 | (JP) . |
| 719360 * | 3/1980 | (SU) . |
| 719630 * | 3/1980 | (SU) . |
| WO 95/23815 | 9/1995 | (WO) . |

* cited by examiner

Primary Examiner—Gollamudi S. Kishore
Assistant Examiner—Lakshmi Channavajjala
(74) Attorney, Agent, or Firm—Oblon, Spivak, McClelland, Maier & Neustadt, P.C.

(57) ABSTRACT

An external skin-care composition comprising (A) a low-strength agar having a jelly strength of 250 g/cm$^2$ or lower as measured at an agar concentration of 1.5 wt. %; (B) a water-soluble polymer; (C) a cooling agent; and (D) water. The external skin-care composition has a high cooling effect, a feeling of coolness and excellent stability.

15 Claims, 1 Drawing Sheet

EXTERNAL SKIN-CARE COMPOSITION

BACKGROUND OF THE INVENTION

1. Field of the Invention

The present invention relates to an external skin-care composition which has a high cooling effect and excellent stability properties.

2. Discussion of Background

Agar has been used for a long time as a food material. Agar is also used as a thickener for cosmetic compositions and drugs for external application.

However, products for external application containing agar as a thickener undergo water separation when they are stored for a long period of time or kept at a high temperature, so that their uses have been limited. For example, a facial preparation for dry skin is disclosed in USSR Patent No. 719630 and contains a rennet ferment, carboxymethyl cellulose, glycerol, ethanol, perfume base and water, where sufficient amounts of neutral proteinase, elastase, collagenase, agar, boric acid, dye and menthol are added for the purpose of improving the skin tissue-softening effect and vital tissue-regenerating effect.

In recent years, agar having high flowability such as the low-strength agar disclosed in Japanese Patent Application Laid-Open No. 56625/1994, has been developed, and are used in cosmetic compositions to improve their properties.

SUMMARY OF THE INVENTION

It is an object of the present invention to provide an external skin-care composition which is stable without undergoing water separation and has an excellent cooling effect, and gives users a pleasant feeling of coolness.

The present inventors have discovered that when an external skin-care composition is prepared by using agar having a specific jelly strength and a water-soluble polymer to provide an aqueous gel, the stability of the system is markedly improved, and an excellent cooling effect based on the high water-retaining ability of the agar can be achieved. The present inventors have also found that when a cooling agent is used in combination with the components described above, the cooling effect can be still more enhanced, thus leading to completion of the present invention.

Accordingly, the present invention provides an external skin-care composition comprising the following components (A), (B), (C) and (D):

(A) low-strength agar having a jelly strength of 250 $g/cm^2$ or lower as measured at an agar concentration of 1.5 wt. % in water;
(B) a water-soluble polymer;
(C) a cooling agent; and
(D) water.

The external skin-care composition according to the present invention has a high cooling effect, a feeling of coolness and excellent stability.

A more complete appreciation of the invention and many of the attendant advantages thereof will be readily obtained as the same becomes better understood by reference to the following detailed description when considered in connection with the accompanying drawings, wherein:

DETAILED DESCRIPTION OF THE INVENTION

Figure 1:
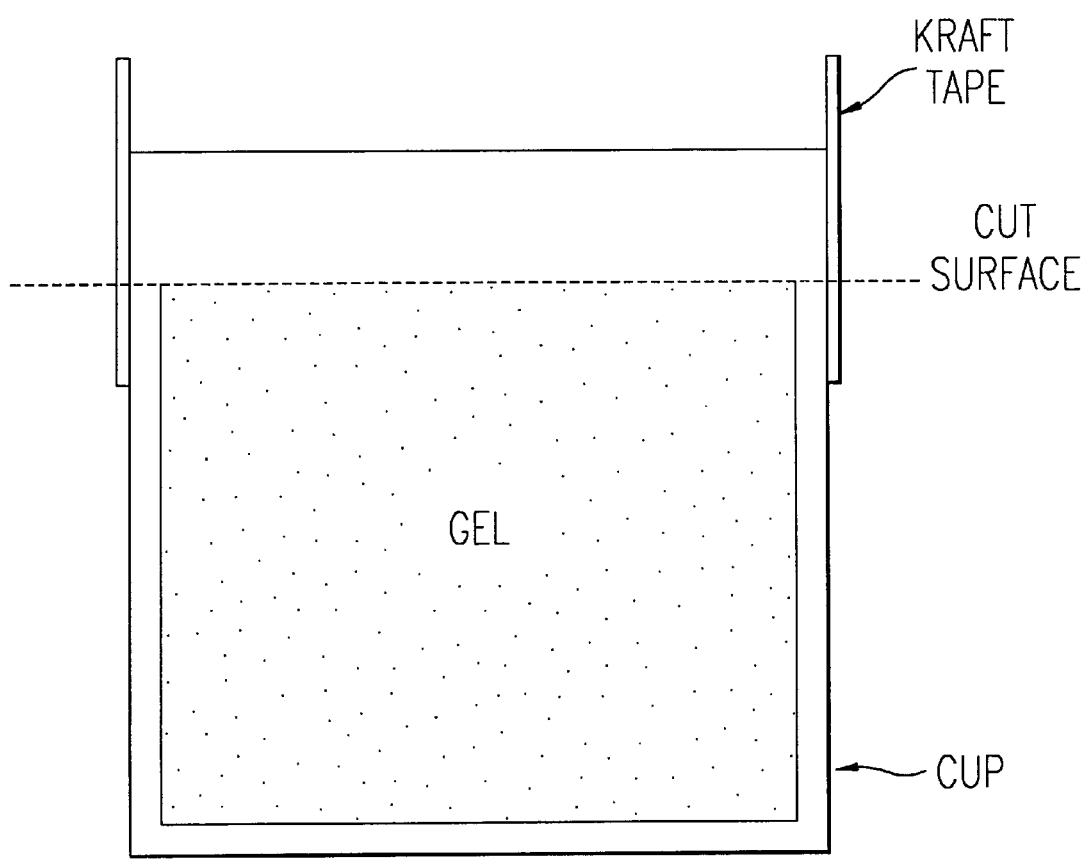
FIG. 1 illustrates a cut surface upon measurement of the jelly strength of agar.

Component (A) useful is a low-strength agar having a jelly strength of 250 $g/cm^2$ or lower as measured at an agar concentration of 1.5% by weight in water. If the jelly strength is higher than 250 $g/cm^2$, the feeling of the resulting external skin-care composition upon use becomes poor. It is preferred that the jelly strength be 50 to 200 $g/cm^2$, particularly 80 to 200 $g/cm^2$. These ranges for the jelly strength include all specific values and subranges therebetween, such as 60, 70, 90, 100, 110, 120, 130, 140, 150, 160, 170, 180 and 190 $g/cm^2$.

The low-strength agar can be obtained, for example, in accordance with the process described in Japanese Patent Application Laid-Open No. 56625/1994, incorporated herein by reference. The jelly strength of the agar is measured in the following manner.

[1] Apparatus and instruments:
  1) Measuring apparatus: Rheometer NRM-200J
     (manufactured by Fudo Kogyo)
       Plunger: cylindrical plunger; area: 1 $cm^2$
       Sample holder lifting rate: 2 cm/min
  2) Glass-made dissolving container (volume: 1.5 L)
  3) Measuring container: plastic cup (inner diameter: 49 mm, depth: 57 mm)
  4) Air conditioning incubator:
  Preset temperature: 20° C.
[2] Measuring method:
  (1) Preparation of 1.5 wt. % aqueous gel:
    1) A sample of agar weighing 9.0 g is prepared.
    2) The sample is placed in the glass-made container the weight of which has been measured beforehand, and ion-exchanged water (100 ml) is added to cause go water to be sufficiently absorbed into the agar.
    3) Hot ion-exchanged water is added to make the total amount of about 650 g.
    4) The container is provided with a lid and placed in a microwave oven to heat the sample for 15 minutes with a heat control dial set at <Strong>position.
    5) The container is taken out of the microwave oven, and the amount of the contents is adjusted to 600.0 g. The aqueous solution is poured into the measuring cup.
    6) When the solution completely gels after leaving the cup in an ambient atmosphere to stand for about 1 hour, the cup is placed in the incubator controlled at 20° C. and held for 15 hours.
  (2) Measurement of jelly strength:
    1) A kraft tape of the measuring container is taken out to cut the gel with a cutter (kitchen knife) (see FIG. 1).
    2) The strength at the cut surface is measured by the rheometer.

The amount of the low-strength agar incorporated into the external skin-care composition according to the present invention is preferably 0.1 to 10% by weight, particularly 1 to 3% by weight based on the total weight of the composition from the viewpoints of the ability to sufficiently retain water in the system, and the solubility and feeling upon use according to the gelation. These ranges for the amount of agar in the composition include all specified values and subranges therebetween, including 0.2, 0.5, 2.5 and 8% by weight.

Examples of the water-soluble polymer (B) useful for the present invention include natural polymers such as xanthan gum, sodium alginate, carrageenan, quince seed gum, hyaluronic acid and pectin; cellulose derivatives such as methyl cellulose, hydroxymethyl cellulose, hydroxyethyl cellulose, hydroxypropyl cellulose and carboxymethyl cellulose; and synthetic polymers such as polyvinyl alcohol, carboxyvinyl polymers, sodium polyacrylate, sodium polymethacrylate, glyceryl polyacrylates and polyvinyl pyrrolidone. Among these, xanthan gum and carboxyvinyl polymers are preferred.

These water-soluble polymers (B) may be used either singly or in any combination thereof. The component (B) is preferably incorporated into the external skin-care composition in a proportion of 1 to 100% by weight, particularly 10 to 100% by weight based on the incorporated amount of the low-strength agar (A) from the viewpoints of the prevention of separation of water from the agar and the cooling effect. Accordingly, the composition may contain 0.001 to 10% by weight of (B). This range includes all specific values and subranges therebetween, such as 0.005, 0.01, 0.02, 0.05, 0.1, 0.5, 1, 2, 3, 4, 5, 6, 7, 8 and 9% by weight.

Examples of the cooling agent (C) useful for the present invention include menthols, camphors and borneols such as l-menthol, dl-menthol, d-camphor, dl-camphor, d-borneol and dl-borneol. Plant extracts containing one or more of these compounds, for example, peppermint oil, peppermint extract, *Perilla frutescens* Britton var. *acuta* Kudo extract, camphor tree extract and lavender extract, may also be used.

These cooling agents (C) may be used either singly or in any combination thereof. The component (C) is preferably incorporated into the external skin-care composition in a proportion of 0.001 to 10% by weight, particularly 0.01 to 1% by weight based on the total weight of the composition from the viewpoints of a good feeling of coolness and low stimulation to the skin. The ranges for the amount of the cooling agent in the composition include all specific values and subranges therebetween, such as 0.005, 0.02, 0.05, 0.1, 0.5, 2, 3, 4, 5, 6, 7, 8 and 9% by weight.

Water (D) is preferably incorporated into the external skin-care composition in a proportion of 10 to 95% by weight, particularly 50 to 90% by weight based on the total weight of the composition. These ranges for the amount of water in the composition include all specific values and subranges therebetween, including 15, 20, 25, 30, 40, 60, 70 and 80% by weight.

In the external skin-care composition according to the present invention, other ingredients commonly used for cosmetics and drugs for external application may be suitably incorporated in addition to the above-described essential components so far as no detrimental influence is thereby imposed on the effects of the present invention. Such additional additives may be, for example, ethanol, oily substances, moisturizers, preservatives, emulsifiers, medicinally effective agents, powders, ultraviolet absorbents, pigments, perfume bases, emulsion stabilizers and pH adjusters. These materials may be used alone or in any suitable combination thereof.

The external skin-care composition according to the present invention can be prepared by mixing the respective components in accordance with a method known per se in the art to provide a skin-care cosmetic composition or a drug for external application in the form of an aqueous gel.

EXAMPLES

Examples 1 to 6 and Comparative Examples 1 to 6

Aqueous gels shown in Table 1 were prepared in accordance with the following process and evaluated. (Preparation process). Water was added to the components (a) and (b), and the mixture was heated to 80° C. to dissolve the components.

After the solution was gradually cooled with stiring, the other components were added to the cooled mixture. The resultant mixture was then deaerated.

Evaluation Methods:

Stability:

Each gel sample was stored for 1 month at 40° C. to visually observe the degree of water separation in accordance with the following standard. The results are shown in Table 1.

Evaluation Standard:

∘: No water separation was observed;

Δ: Water slightly exuded;

×: Water exuded.

Feeling Upon Use:

Each gel sample was applied to the face of each of 20 female panelists after washing to organoleptically evaluate in accordance with the following standard. The results are shown in Table 1.

Evaluation Standard:

∘: At least 16 panelists answered that the gel gave a feeling of coolness;

Δ: 6 to 15 panelists answered that the gel gave a feeling of coolness;

×: At most 5 panelists answered that the gel gave a feeling of coolness.

Cooling Effect:

Each gel sample was applied to half the face of each of 20 female panelists after washing, and the skin temperature thereof was measured after left to stand for 1 minute at a temperature of 20° C. and a relative humidity of 40%, whereby the cooling effect of the gel was evaluated by a difference in temperature between the applied part and an unapplied part. The results are shown in Table 1.

TABLE 1

|  | Invention Product | | | | | | Comparative Product | | | | | |
| --- | --- | --- | --- | --- | --- | --- | --- | --- | --- | --- | --- | --- |
|  | 1 | 2 | 3 | 4 | 5 | 6 | 1 | 2 | 3 | 4 | 5 | 6 |
| (A) | | | | | | | | | | | | |
| Agar* | 1.50 | 1.50 | 2.00 | 2.00 | 1.50 | 1.50 | 1.50 | — | 1.50 | 1.50 | 1.50 (a) | 1.50 (b) |
| (B) | | | | | | | | | | | | |
| xanthan gum | 0.30 | 0.0 | 0.50 | 0.30 | — | 0.50 | — | 0.50 | — | 0.50 | 0.30 | 0.30 |
| Carboxyvinyl polymer | — | — | — | — | 0.10 | — | — | — | — | — | — | — |
| (C) | | | | | | | | | | | | |
| -Menthol | 0.01 | 0.01 | 0.01 | 0.01 | 0.01 | — | — | 0.01 | 0.01 | — | 0.01 | 0.01 |
| Peppermint oil | — | — | — | — | — | 0.01 | — | — | — | — | — | — |
| 55% Ethanol | 5.00 | 5.00 | 5.00 | 5.00 | 5.00 | 5.00 | 5.00 | 5.00 | 5.00 | 5.00 | 5.00 | 5.00 |
| Glycerol | 10.00 | 10.00 | 10.00 | 10.00 | 10.00 | 10.00 | 10.00 | 10.00 | 10.00 | 10.00 | 10.00 | 10.00 |
| Methylparaben | 0.10 | 0.10 | 0.10 | 0.10 | 0.10 | 0.10 | 0.10 | 0.10 | 0.10 | 0.10 | 0.10 | 0.10 |
| Sodium citrate | 0.10 | 0.10 | 0.10 | 0.10 | 0.10 | 0.10 | 0.10 | 0.10 | 0.10 | 0.10 | 0.10 | 0.10 |
| Purified water | Bal. | Bal. | Bal. | Bal. | Bal. | Bal. | Bal. | Bal. | Bal. | Bal. | Bal. | Bal. |
| Evaluation: | | | | | | | | | | | | |
| Stability | ○ | ○ | ○ | ○ | ○ | ○ | X | ○ | X | ○ | X | X |
| Feeling of coolness | ○ | ○ | ○ | ○ | ○ | ○ | Δ | Δ | ○ | Δ | Δ | X |
| Cooling effect (C) | −2.5 | −2.5 | −2.5 | −2.5 | −2.5 | −2.4 | −2.3 | −0.5 | −2.6 | −2.1 | −1.0 | −0.5 |

*: Agar used in Examples 1 to 6 and Comparative Examples 1 to 4: Ultra Agar Ax-100 (trade name; product of Ina Shokuhin K. K.; jelly strength of 1.5 wt. % agar: 100 ± 20 g(cm$^2$))
(a): Agar S-5 (trade name; product of Ina Shokuhin K. K.; jelly strength of 1.5 wt. % agar: 530 ± 20 g/cm$^2$)
(b): Agar (S-8 (trade name; product of Ina Shokuhin K. K.; jelly strength of 1.5 wt. % agar: 830 ± 20 g/cm$^2$)

Examples 7 to 10

(Cream)

Creams shown in Table 2 were prepared in accordance with the following process.

Preparation Process:

The components (i) were stirred at 80° C. for 30 minutes to disperse them. The oil-phase components (ii) were heated to 70° C. to melt them. The water-phase components (iii) heated to 70° C. were added to the above molten oil-phase components (ii) with stirring to emulsify them. The resultant emulsion was then cooled down to 60° C. with stirring. The components (i) cooled down to 60° C. and the components (iv) were then added to the emulsion, and the resultant mixture was cooled down to room temperature with stirring.

The thus-obtained creams were all excellent in a feeling of coolness, cooling effect and stability.

TABLE 2

|  |  | Invention Product | | | |
| --- | --- | --- | --- | --- | --- |
|  |  | 7 | 8 | 9 | 10 |
| (i) | Agar* | 1.50 | 1.50 | 1.50 | 1.50 |
|  | Xanthan gum | 0.50 | — | 0.50 | — |
|  | Carboxyvinyl polymer | — | 0.50 | — | 0.50 |
|  | Purified water | 30.00 | 30.00 | 30.00 | 30.00 |
| (ii) | Decaglyceryl stearate | 1.80 | 1.80 | 1.80 | 1.80 |
|  | Polyoxyethylene cetyl ether | 1.20 | 1.20 | 1.20 | 1.20 |
|  | Squalane | 12.00 | 12.00 | 12.00 | 12.00 |
|  | Cetanol | 6.00 | 6.00 | 6.00 | 6.00 |
|  | Cetyl palmitate | 3.00 | 3.00 | 3.00 | 3.00 |
|  | 1,3-Butylene glycol | 6.00 | 6.00 | 6.00 | 6.00 |
| (iii) | Glycerol | 10.00 | 10.00 | 10.00 | 10.00 |
|  | Methylparaben | 0.10 | 0.10 | 0.10 | 0.10 |
|  | Sodium citrate | 0.10 | 0.10 | 0.10 | 0.10 |
|  | Preservative | q.s. | q.s. | q.s. | q.s. |
|  | Purified water | Bal. | Bal. | Bal. | Bal. |
| (iv) | 1-Menthol | 0.10 | 0.10 | — | — |
|  | peppermint oil | — | — | 0.10 | 0.10 |
|  | 55% Ethanol | 5.00 | 5.00 | 5.00 | 5.00 |

*Ultra Agar Ax-100 (trade name; product of Ina Shokuhin K.K.; jelly strength of 1.5 wt. % agar: 100 ± 20 g/cm$^2$)

Cosmetic emulsions shown in Table 3 were prepared in accordance with the following process.

Preparation Process:

The components (i) were stirred at 80° C. for 30 minutes to disperse them. The oil-phase components (ii) were heated to 70° C. to melt them. The water-phase components (iii) heated to 70° C. were added to the above molten oil-phase components (ii) with stirring to emulsify them. The resultant emulsion was then cooled down to 60° C. with stirring. The components (i) cooled down to 60° C. and the components (iv) were then added to the emulsion, and the resultant mixture was cooled down to room temperature with stirring.

The thus-obtained cosmetic emulsions were all excellent in a feeling of coolness, cooling effect and stability.

TABLE 3

|  |  | Invention Product | | | |
| --- | --- | --- | --- | --- | --- |
|  |  | 11 | 12 | 13 | 14 |
| (i) | Agar* | 1.50 | 1.50 | 1.50 | 1.50 |
|  | Xanthan gum | 0.50 | 0.50 | 0.50 | — |

TABLE 3-continued

| | | Invention Product | | | |
|---|---|---|---|---|---|
| | | 11 | 12 | 13 | 14 |
| | Carboxyvinyl polymer | — | — | — | 0.50 |
| | Purified water | 30.00 | 30.00 | 30.00 | 30.00 |
| (ii) | Cetanol | 1.00 | 1.00 | 1.00 | 1.00 |
| | Squalane | 5.00 | — | — | — |
| | Vaseline | 2.00 | 1.00 | 1.00 | 1.00 |
| | Lanolin alcohol | 2.00 | 0.50 | 0.50 | 0.50 |
| | Stearic acid | 2.00 | 6.00 | 6.00 | 6.00 |
| | Polyoxyethylene (20) sorbitan monolaurate | 2.00 | 2.00 | 2.00 | 2.00 |
| (iii) | Glycerol | 10.00 | 10.00 | 10.00 | 10.00 |
| | Methylparaben | 0.10 | 0.10 | 0.10 | 0.10 |
| | Sodium citrate | 0.10 | 0.10 | 0.10 | 0.10 |
| | Preservative | q.s. | q.s. | q.s. | q.s. |
| | Purified water | Bal. | Bal. | Bal. | Bal. |
| (iv) | 1-Menthol | 0.10 | 0.10 | — | 0.10 |
| | peppermint oil | — | — | 0.10 | — |
| | 55% Ethanol | 5.00 | 5.00 | 5.00 | 5.00 |

*Ultra Agar Ax-100 (trade name; product of Ina Shokuhin K.K.; jelly strength of 1.5 wt. % agar: 100 ± 20 g/cm$^2$)

Obviously, additional modifications and variations of the present invention are possible in light of the above teachings. It is therefore to be understood that within the scope of the appended claims, the invention may be practiced otherwise than as specifically described herein.

Japanese Patent Application No. 9-295433, filed on Oct. 28, 1997, is incorporated herein by reference in its entirety.

What is claimed as new and desired to be secured by Letters Patent of the United States is:

1. An external skin-care composition comprising:
   (A) at least 1.5 wt. % low-strength agar having a jelly strength of at most 250 g/cm$^2$, as measured at an agar concentration of 1.5 wt. % in water;
   (B) 0.1 to 10 wt. % water soluble polymer which is xanthan gum or a carboxyvinyl polymer;
   (C) at least 0.01% wt. % of a cooling agent selected from the group consisting of: menthols, camphors, borneols, and plant extracts containing one or more of these compounds; and
   (D) water.

2. The external skin-care composition according to claim 1, wherein the cooling agent (C) comprises a plant extract containing a compound selected from the group consisting of a menthol, a camphor and a borneol.

3. The external skin-care composition according to claim 1, wherein the content of the low-strength agar (A) is 1.5 to 10 wt. % based on the total weight of the composition, and the content of the water-soluble polymer (B) is 10 to 100 wt. % based on the content of the component (A).

4. The external skin-care composition of claim 1, wherein the agar has a jelly strength of 50 to 250 g/cm$^2$.

5. The external skin-care composition of claim 1, wherein the agar has a jelly strength of 50 to 200 g/cm$^2$.

6. The external skin-care composition of claim 1, wherein the agar has a jelly strength of 80 to 200 g/cm$^2$.

7. The external skin-care composition of claim 1, further comprising at least one additive selected from the group consisting of ethanol, oily substances, moisturizers, preservatives, emulsifiers, medicinally effective agents, powders, ultraviolet absorbents, pigments, perfume bases, emulsion stabilizers and pH adjusters.

8. The external skin-care composition of claim 1, which is in the form of a gel.

9. The external skin care composition of claim 1, comprising:
   1.5 to 10% by weight of (A);
   0.1 to 10% by weight of (B); and
   0.01 to 10% by weight of (C).

10. The external skin-care composition of claim 9, wherein the agar has a jelly strength of 50 to 250 g/cm$^2$.

11. The external skin-care composition of claim 9, wherein the agar has a jelly strength of 80 to 200 g/cm$^2$.

12. The external skin-care composition of claim 9, further comprising at least one additive selected from the group consisting of ethanol, oily substances, moisturizers, preservatives, emulsifiers, medicinally effective agents, powders, ultraviolet absorbents, pigments, perfume bases, emulsion stabilizers and pH adjusters.

13. The external skin-care composition of claim 9, which is in the form of a gel.

14. A method of providing a cooling sensation to skin, comprising applying an effective amount of the composition of claim 1 to the skin.

15. A method of preparing the external skin-care composition of claim 1, comprising combining said (A), (B), (C) and (D).

* * * * *